United States Patent
Huelskamp et al.

(10) Patent No.: US 11,896,472 B2
(45) Date of Patent: Feb. 13, 2024

(54) SURGICAL MESH HAVING INGROWTH-PREVENTING COATING ON ONE SIDE THEREOF, AND METHOD FOR MAKING THE SAME

(71) Applicant: Grant Technologies LLC, Barrington, IL (US)

(72) Inventors: John W. Huelskamp, Barrington, IL (US); Andrew R. Leopold, North Barrington, IL (US)

(73) Assignee: Grant Technologies LLC, Barrington, IL (US)

( * ) Notice: Subject to any disclaimer, the term of this patent is extended or adjusted under 35 U.S.C. 154(b) by 416 days.

(21) Appl. No.: 17/082,534

(22) Filed: Oct. 28, 2020

(65) Prior Publication Data
US 2021/0121279 A1 Apr. 29, 2021

Related U.S. Application Data

(60) Provisional application No. 62/926,618, filed on Oct. 28, 2019.

(51) Int. Cl.
*A61F 2/00* (2006.01)

(52) U.S. Cl.
CPC .... *A61F 2/0063* (2013.01); *A61F 2210/0004* (2013.01); *A61F 2240/001* (2013.01)

(58) Field of Classification Search
CPC ........... A61F 2/0063; A61L 31/06; C09J 7/40; A61B 17/00234
See application file for complete search history.

(56) References Cited

U.S. PATENT DOCUMENTS

| | | |
|---|---|---|
| 751,415 A | 2/1904 | Prindle |
| 2,330,693 A | 9/1943 | Erdely |
| 4,333,471 A | 6/1982 | KuNakaigel |
| 5,264,218 A | 11/1993 | Rogozinski |
| 5,634,931 A | 6/1997 | Kugel |
| 5,769,864 A | 6/1998 | Kugel |
| 5,795,584 A * | 8/1998 | Totakura ................ A61L 31/06 424/78.37 |
| D399,965 S | 10/1998 | Laughlin et al. |
| 5,916,225 A | 6/1999 | Kugel |
| D416,327 S | 11/1999 | Kugel |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,224,616 B1 | 5/2001 | Kugel |
| D445,188 S | 7/2001 | Walter |

(Continued)

FOREIGN PATENT DOCUMENTS

| | | |
|---|---|---|
| CA | 2201439 | 7/2004 |
| EP | 0783270 | 6/2004 |

(Continued)

*Primary Examiner* — Dah-Wei D. Yuan
*Assistant Examiner* — Andrew J Bowman
(74) *Attorney, Agent, or Firm* — Pandiscio & Pandiscio

(57) ABSTRACT

A coated surgical mesh, the coated surgical mesh comprising: a surgical mesh, the surgical mesh comprising a first surface and a second surface; and a tissue ingrowth-preventing coating applied to the second surface of the surgical mesh; wherein the tissue ingrowth-preventing coating penetrates a controllable amount part way through the surgical mesh.

28 Claims, 19 Drawing Sheets

(56) References Cited

U.S. PATENT DOCUMENTS

| | | |
|---|---|---|
| 6,280,453 B1 | 8/2001 | Kugel et al. |
| 6,290,708 B1 | 9/2001 | Kugel et al. |
| 6,420,622 B1 | 7/2002 | Johnston et al. |
| 6,544,167 B2 | 4/2003 | Buckberg et al. |
| 6,669,735 B1 | 12/2003 | Pelissier |
| 6,790,213 B2 | 9/2004 | Cherok et al. |
| 6,800,082 B2 | 10/2004 | Rousseau |
| 6,884,212 B2 | 4/2005 | Thierfelder et al. |
| 7,396,975 B2 | 7/2008 | Sigurjonsson et al. |
| 8,182,545 B2 | 5/2012 | Cherok et al. |
| 8,562,633 B2 | 10/2013 | Cully et al. |
| D734,458 S | 7/2015 | Huelskamp et al. |
| 9,072,586 B2 | 7/2015 | Ranucci et al. |
| 9,308,068 B2 | 4/2016 | Spinnler et al. |
| D772,410 S | 11/2016 | Huelskamp et al. |
| 9,820,837 B2 | 11/2017 | Cardinale et al. |
| 9,980,802 B2 | 5/2018 | Bailly et al. |
| 10,245,135 B2 | 4/2019 | Huelskamp et al. |
| 10,342,650 B2 | 7/2019 | Russo et al. |
| 10,449,027 B2 | 10/2019 | Griffin et al. |
| 2002/0028980 A1* | 3/2002 | Thierfelder ...... A61B 17/00234 600/30 |
| 2002/0052649 A1 | 5/2002 | Greenhalgh |
| 2003/0130745 A1 | 7/2003 | Cherok et al. |
| 2003/0212460 A1 | 11/2003 | Darois et al. |
| 2005/0123704 A1* | 6/2005 | Sakai ...................... C09J 7/40 442/99 |
| 2007/0276487 A1 | 11/2007 | Carteron et al. |
| 2007/0299538 A1 | 12/2007 | Roeber |
| 2008/0147099 A1 | 6/2008 | Uen |
| 2011/0288567 A1 | 11/2011 | Ranucci et al. |
| 2012/0232334 A1 | 9/2012 | Bell et al. |
| 2013/0218125 A1 | 8/2013 | Stopek et al. |
| 2013/0267970 A1 | 10/2013 | Cardinale et al. |
| 2019/0099252 A1 | 4/2019 | Nelson et al. |

FOREIGN PATENT DOCUMENTS

| | | |
|---|---|---|
| EP | 2730297 | 5/2014 |
| WO | WO 2002/032346 | 4/2002 |
| WO | WO 2010/039249 | 4/2010 |

\* cited by examiner

PLACEMENT OF THE FRAME

EXAMPLE OF A BAD SILICONE AREA

SLIDING THE PTFE ONTO THE OVEN RACK

SURGICAL MESH HAVING INGROWTH-PREVENTING COATING ON ONE SIDE THEREOF, AND METHOD FOR MAKING THE SAME

REFERENCE TO PENDING PRIOR PATENT APPLICATION

This patent application claims benefit of pending prior U.S. Provisional Patent Application Ser. No. 62/926,618, filed Oct. 28, 2019 by Grant Technologies LLC and John W. Huelskamp et al. for SURGICAL MESH HAVING INGROWTH-PREVENTING COATING ON ONE SIDE THEREOF, AND METHOD FOR MAKING THE SAME (Attorney's Docket No. GRANT-8 PROV), which patent application is hereby incorporated herein by reference.

FIELD OF THE INVENTION

This invention relates to medical procedures and apparatus in general, and more particularly to medical procedures and apparatus for repairing soft tissue defects such as inguinal and abdominal wall hernias and the like.

BACKGROUND OF THE INVENTION

In the reconstruction of soft tissue defects in humans and animals, such as in abdominal hernia repairs, surgical mesh is often used to reinforce the soft tissue defect so as to reinforce the abdominal wall, facilitate healing and prevent subsequent defect recurrence. More particularly, when performing a closure of a soft tissue defect in an anatomical wall (e.g., to repair an abdominal hernia), it is common to secure a surgical mesh to the soft tissue at the edge of the soft tissue defect, with some overlap between the surgical mesh and the soft tissue, so as to increase the healed strength of the surgical repair. The surgical mesh is typically secured to the soft tissue adjacent to the soft tissue defect with suture or surgical tacks.

It is common to form the surgical mesh out of a knitted/woven material or a non-knitted/non-woven material.

More particularly, and looking first at FIG. 1, there is shown a knitted/woven surgical mesh 5 which generally comprises a porous knitted/woven material 10 for effecting a tissue repair. Knitted/woven surgical mesh 5 generally comprises a first surface 12 which is intended to be adhered to tissue (e.g., to an abdominal wall, in the case of a hernia mesh), and a second surface 13 which is intended to face away from the tissue to which the surgical mesh is adhered (e.g., to face toward an abdominal cavity, in the case of a hernia mesh). By way of example but not limitation, porous knitted/woven material 10 may comprise a matrix of synthetic fibers (e.g., polypropylene) woven together.

Looking next at FIG. 2, there is shown a non-knitted/non-woven surgical mesh 15 which generally comprises a porous non-knitted/non-woven material 20. Non-knitted/non-woven surgical mesh 15 generally comprises a first surface 22 which is intended to be adhered to tissue (e.g., to an abdominal wall, in the case of a hernia mesh), and a second surface 23 which is intended to face away from the tissue to which the surgical mesh is adhered (e.g., to face toward an abdominal cavity, in the case of a hernia mesh). By way of example but not limitation, porous non-knitted/non-woven material 20 may comprise a matrix of synthetic fibers (e.g., polypropylene) fused together (e.g., at 25) by a point-bonding fusing process (e.g., by point-bonding melting) so as to form a composite structure. In this respect it will be appreciated that the compressive heat process typically leaves a plurality of regularly-spaced recesses 30 which extend partially into, but not all of the way through, the thickness of porous non-knitted/non-woven material 20. It should be appreciated that these recesses 30, extending partially into, but not all the way through, the thickness of the porous non-knitted/non-woven material, constitute only a small percentage of the total surface area of the porous non-knitted/non-woven material. Note that the porous non-knitted/non-woven material 20 disposed at recesses 30 (e.g., at 25) typically has a higher density than the remainder of the porous non-knitted/non-woven material, since the porous non-knitted/non-woven material has been compacted and melted in this region of the porous non-knitted/non-woven material.

In practice, it has been found that it is often desirable to configure the surgical mesh so that it will encourage tissue ingrowth into one side of the surgical mesh (e.g., the abdominal wall side of the surgical mesh) while preventing tissue ingrowth into the opposite side of the surgical mesh (e.g., the abdominal cavity side of the surgical mesh). To this end, it is common to apply an ingrowth-preventing coating formed out of a permanent or resorbable non-porous flexible material (e.g., an elastomer such as silicone or urethane or a flexible resorbable material) to one side of the surgical mesh so that the ingrowth-preventing coating closes off the pores of the mesh (e.g., in the case of a knitted/woven mesh, the pores of the knitted/woven material forming the mesh, and in the case of a non-knitted/non-woven mesh, the pores between the polypropylene fibers, and also the recesses 30 of the non-knitted/non-woven material forming the mesh). See, for example, FIG. 3, where an ingrowth-preventing coating 35 (e.g., a permanent or resorbable non-porous flexible coating such as silicone, urethane, a flexible resorbable material, etc.) is applied to second surface 13 of knitted/woven surgical mesh 5 (e.g., the abdominal cavity side of the knitted/woven surgical mesh), in order to prevent adhesion of internal organs to the surgical mesh and thus creating a barrier surgical mesh. See also, for example, FIG. 4, where an ingrowth-preventing coating 35 (e.g., a permanent or resorbable non-porous flexible coating such as silicone, urethane, a flexible resorbable material, etc.) is applied to second surface 23 of non-knitted/non-woven surgical mesh 15 (e.g., the surface of the non-knitted/non-woven surgical mesh 15 which faces the abdominal cavity) in order to prevent adhesion of internal organs to the surgical mesh and thus creating a barrier surgical mesh.

In practice, ingrowth-preventing coating 35 (e.g., a permanent or resorbable non-porous flexible coating such as silicone, urethane, a flexible resorbable material, etc.) is commonly applied to knitted/woven surgical mesh 5, and/or to non-knitted/non-woven surgical mesh 15, using a mechanical compression process such as calendaring, where the ingrowth-preventing coating is applied as a liquid to one side of the surgical mesh (i.e., second surface 13 of knitted/woven surgical mesh 5 and/or second surface 23 of non-knitted/non-woven surgical mesh 15), then the surgical mesh is passed through rollers so as to cause the ingrowth-preventing coating to penetrate into the surgical mesh, and then the combined surgical mesh and ingrowth-preventing coating are exposed to a curing process in order convert the ingrowth-preventing coating to a solid form and secure the ingrowth-preventing coating to the surgical mesh.

While the mechanical compression process is effective in applying/fixing ingrowth-preventing coating 35 (e.g., a permanent or resorbable non-porous flexible coating such as silicone, urethane, a flexible resorbable material, etc.) to the surgical mesh, it has been found that the mechanical compression process causes the ingrowth-preventing coating to penetrate into the surgical mesh in an irregular fashion, i.e., ingrowth-preventing coating 35 penetrates irregularly into porous knitted/woven material 10 of knitted/woven surgical mesh 5 (FIG. 3) and/or into the porous non-knitted/non-woven material 20 of non-knitted/non-woven surgical mesh 15 (FIG. 4). In some cases, and as seen in FIGS. 3 and 4, ingrowth-preventing coating 35 (e.g., a permanent or resorbable non-porous flexible coating such as silicone, urethane, a flexible resorbable material, etc.) may penetrate all the way through the surgical mesh (e.g., such as is shown at 40) to first surface 12 of surgical mesh 5 (i.e., the surface of knitted/woven surgical mesh 5 which faces the abdominal wall) and/or to first surface 22 of non-knitted/non-woven surgical mesh 15 (i.e., the surface of non-knitted/non-woven surgical mesh 15 which faces the abdominal wall). Where this occurs, ingrowth-preventing coating 35 (e.g., a permanent or resorbable non-porous flexible coating such as silicone, urethane, a flexible resorbable material, etc.) prevents tissue ingrowth on the abdominal wall side of the surgical mesh (i.e., tissue ingrowth into first surface 12 of knitted/woven surgical mesh 5 and/or tissue ingrowth into first surface 22 of non-knitted/non-woven surgical mesh 15), reducing the integration of the surgical mesh into the surrounding tissues and potentially leading to hernia recurrence.

Thus there is a need for a new and improved approach for applying an ingrowth-preventing coating (which is permanent or resorbable, and adhesion-preventing) on one side of a surgical mesh (e.g., on the abdominal cavity side of a surgical mesh) while ensuring that the ingrowth-preventing coating does not penetrate through to the other side of the surgical mesh (e.g., the abdominal wall side of the surgical mesh) and supports adjacent improved tissue integration at the desired locations.

SUMMARY OF THE INVENTION

The present invention comprises a new and improved approach for applying an ingrowth-preventing coating (which is permanent or resorbable, and adhesion-preventing) on one side of a surgical mesh (e.g., on the abdominal cavity side of a surgical mesh) while ensuring that the ingrowth-preventing coating does not penetrate through to the other side of the surgical mesh (e.g., the abdominal wall side).

In one preferred form of the present invention, there is provided a coated surgical mesh, said coated surgical mesh comprising:

a surgical mesh, said surgical mesh comprising a first surface and a second surface; and a tissue ingrowth-preventing coating applied to said second surface of said surgical mesh;

wherein said tissue ingrowth-preventing coating penetrates only part way through said surgical mesh.

In one form of the invention, the surgical mesh comprises a porous knitted/woven material. In another form of the invention, the surgical mesh comprises a porous non-knitted/non-woven material.

In one form of the invention, the ingrowth-preventing coating is applied to the surgical mesh as a liquid, and is thereafter cured so as to convert the ingrowth-preventing coating to a solid form which adheres to the surgical mesh.

In one form of the invention, the ingrowth-preventing coating penetrates into the pores of the surgical mesh while the ingrowth-preventing coating is in a liquid state, and is thereafter cured to a solid state so that the ingrowth-preventing coating mechanically interlocks with the surgical mesh so that the ingrowth-preventing coating and the surgical mesh together form the coated surgical mesh.

In another preferred form of the present invention, there is provided a method of manufacturing a coated surgical mesh, said method comprising:

providing a surgical mesh, said surgical mesh comprising a first surface and a second surface; and positioning said second surface of said surgical mesh on a tissue ingrowth-preventing coating such that said tissue ingrowth-preventing coating penetrates into said surgical mesh part way, but not all of the way, through said surgical mesh.

In one form of the invention, the surgical mesh comprises a porous knitted/woven material. In another form of the invention, the surgical mesh comprises a porous non-knitted/non-woven material.

In one form of the invention, the ingrowth-preventing coating is applied to the surgical mesh as a liquid, and is thereafter cured so as to convert the ingrowth-preventing coating to a solid form which adheres to the surgical mesh.

In one form of the invention, the ingrowth-preventing coating penetrates into the pores of the surgical mesh while the ingrowth-preventing coating is in a liquid state, and is thereafter cured to a solid state so that the ingrowth-preventing coating mechanically interlocks with the surgical mesh so that the ingrowth-preventing coating and the surgical mesh together form the coated surgical mesh.

In one form of the invention, there is provided a method of manufacturing a coated surgical mesh, said method comprising:

providing a surgical mesh comprising a first surface and a second surface;

providing a release sheet;

positioning an ingrowth-preventing coating onto the release sheet;

placing the second surface of the surgical mesh onto the ingrowth-preventing coating;

applying pressure to the first surface of the surgical mesh so that the ingrowth-preventing coating is forced into the surgical mesh without penetrating all the way through the surgical mesh;

curing the ingrowth-preventing coating so as to fuse the ingrowth-preventing coating to the surgical mesh, whereby to form the coated surgical mesh; and removing the coated surgical mesh from the release sheet.

In another form of the invention, there is provided a method of manufacturing a coated surgical mesh, said method comprising:

providing a surgical mesh comprising a first surface and a second surface, wherein the surgical mesh comprises a non-knitted/non-woven material;

providing a release sheet;

positioning an ingrowth-preventing coating comprising a liquid dispersion of silicone onto the release sheet using an applicator;

allowing the ingrowth-preventing coating to evaporate for a period of time;

placing the second surface of the surgical mesh onto the ingrowth-preventing coating;

using a flattening piece to lightly slide the surgical mesh around the ingrowth-preventing coating without pushing down on the surgical mesh;

applying pressure to the first surface of the surgical mesh so that the ingrowth-preventing coating is forced into the surgical mesh without penetrating all the way through the surgical mesh to the first surface of the surgical mesh;

curing the ingrowth-preventing coating so as to fuse the ingrowth-preventing coating to the surgical mesh, whereby to form the coated surgical mesh;

removing the coated surgical mesh from the release sheet; and trimming around the coated surgical mesh.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises a new and improved approach for applying an ingrowth-preventing coating (which is permanent or resorbable, and adhesion-preventing) on one side of a surgical mesh (e.g., on the abdominal cavity side of a surgical mesh) while ensuring that the ingrowth-preventing coating does not penetrate through to the other side of the surgical mesh (e.g., the abdominal wall side of the surgical mesh).

Figure 1:
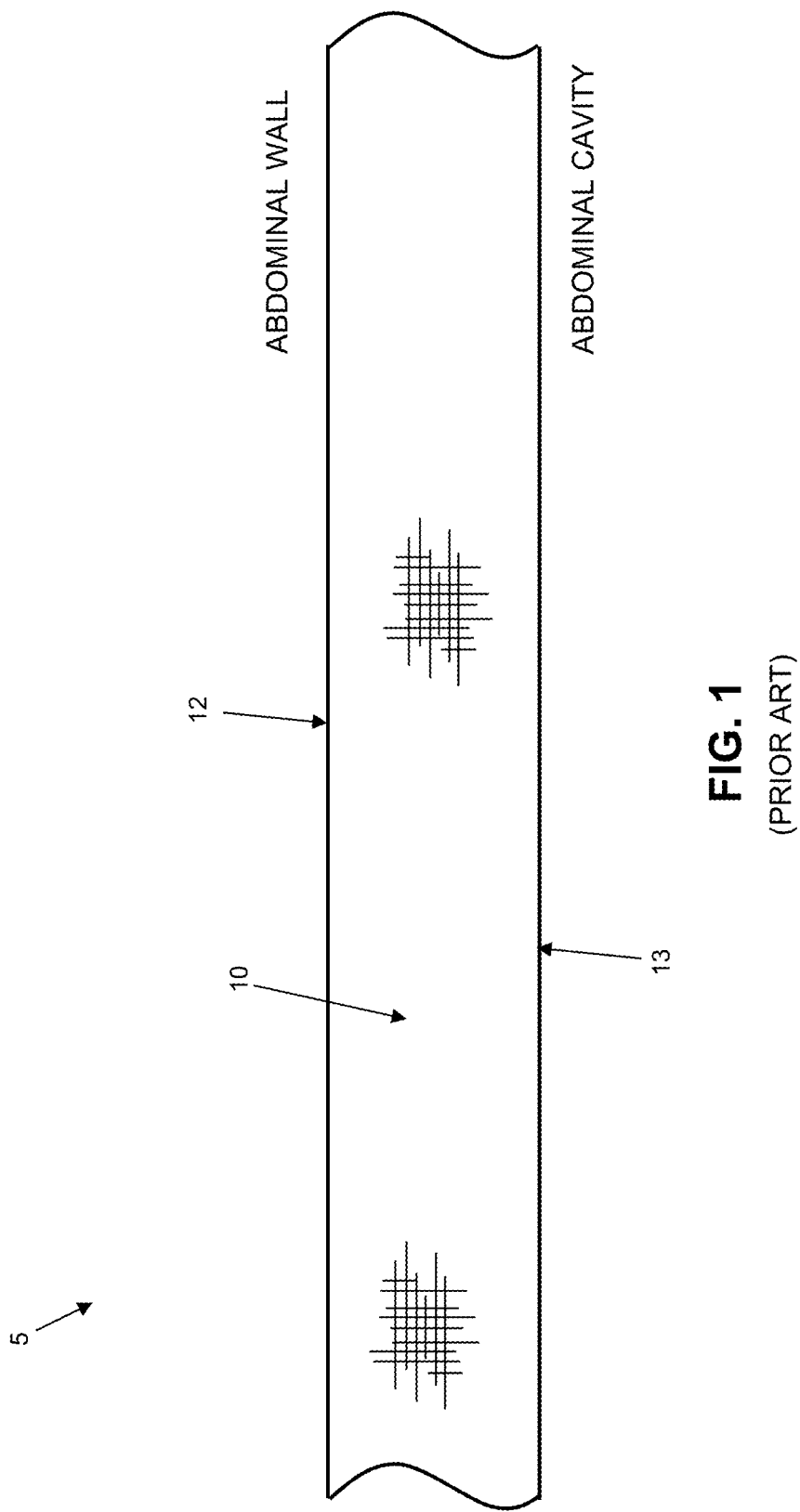
FIG. 1 is a schematic view showing an exemplary prior art knitted/woven surgical mesh.
Figure 2:
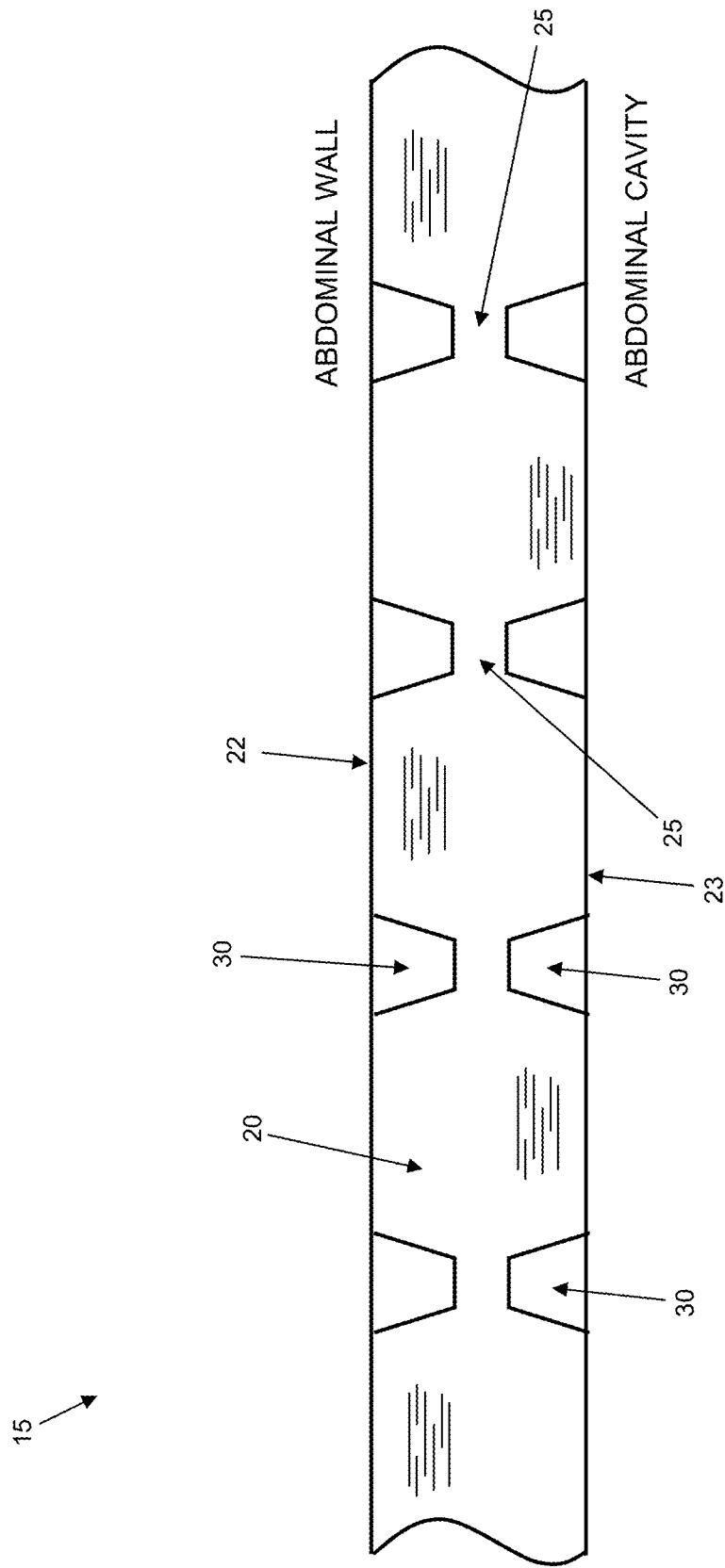
FIG. 2 is a schematic view showing an exemplary prior art non-knitted/non-woven surgical mesh.
Figure 3:
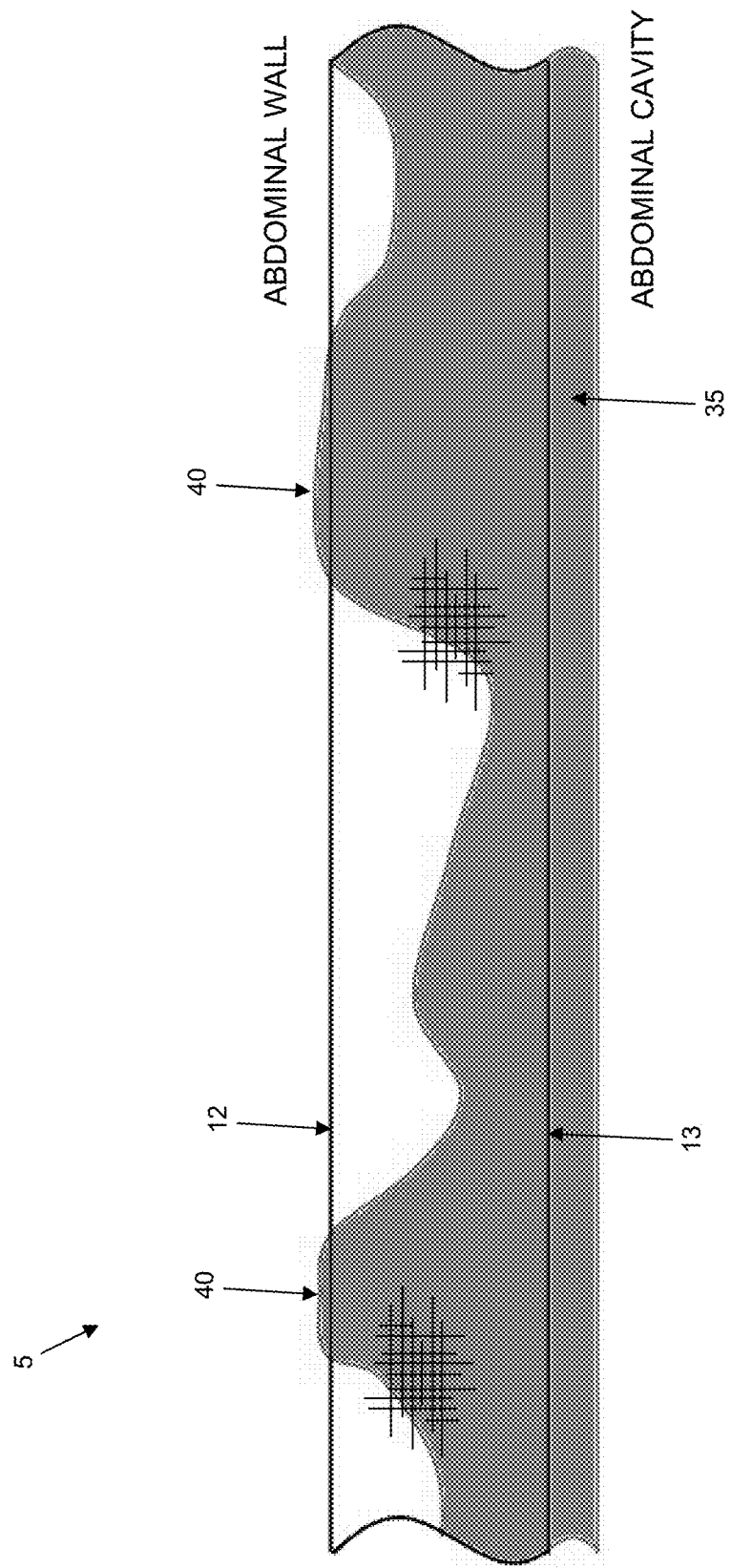
FIG. 3 is a schematic view showing a prior art coated knitted/woven surgical mesh having an ingrowth-preventing coating on one side of the knitted/woven surgical mesh, wherein the ingrowth-preventing coating penetrates completely through the knitted/woven surgical mesh in some locations.
Figure 4:
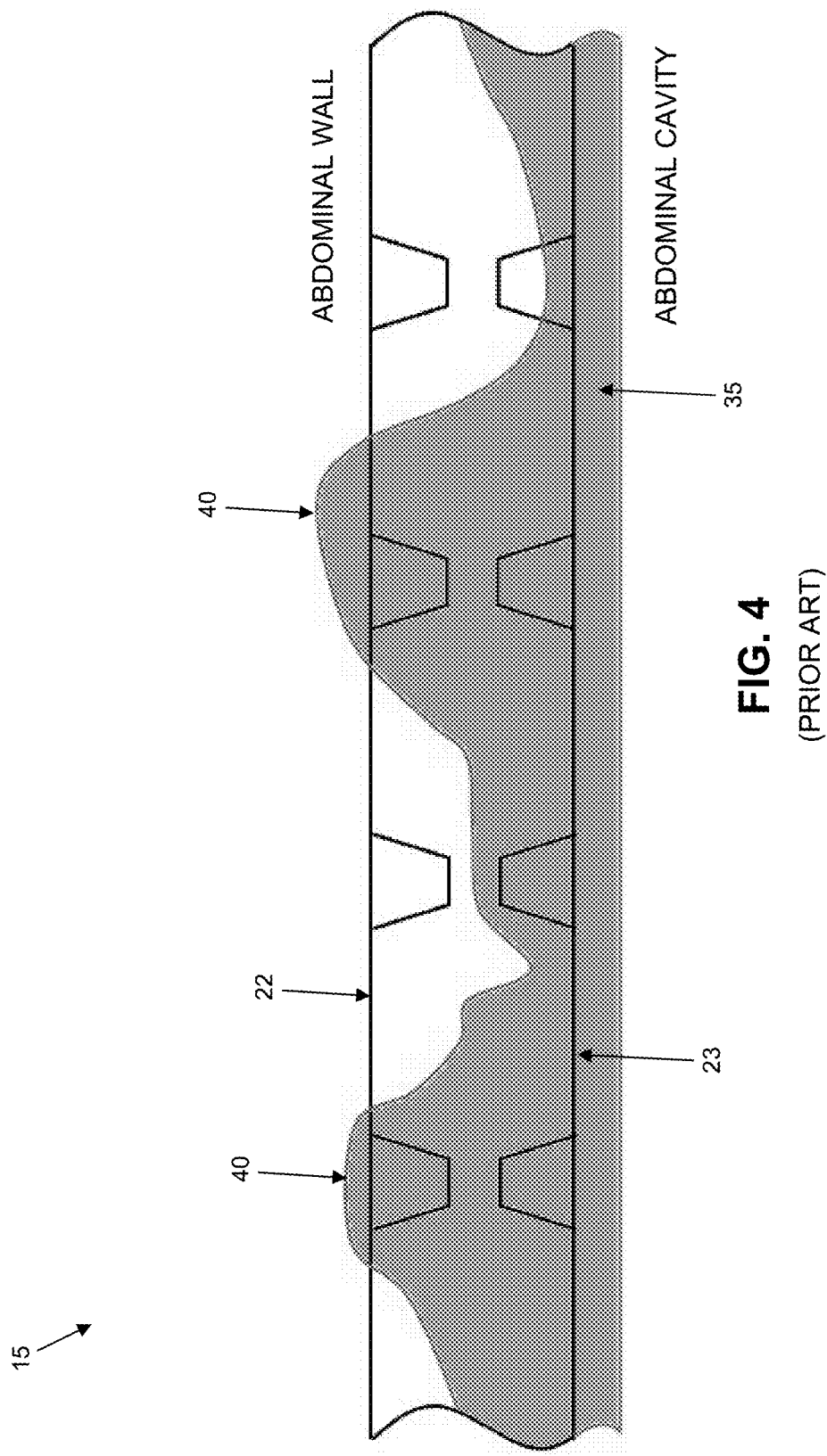
FIG. 4 is a schematic view showing a prior art coated non-knitted/non-woven surgical mesh having an ingrowth-preventing coating on one side of the non-knitted/non-woven surgical mesh, wherein the ingrowth-preventing coating penetrates completely through the non-knitted/non-woven surgical mesh in some locations.
Figure 5:
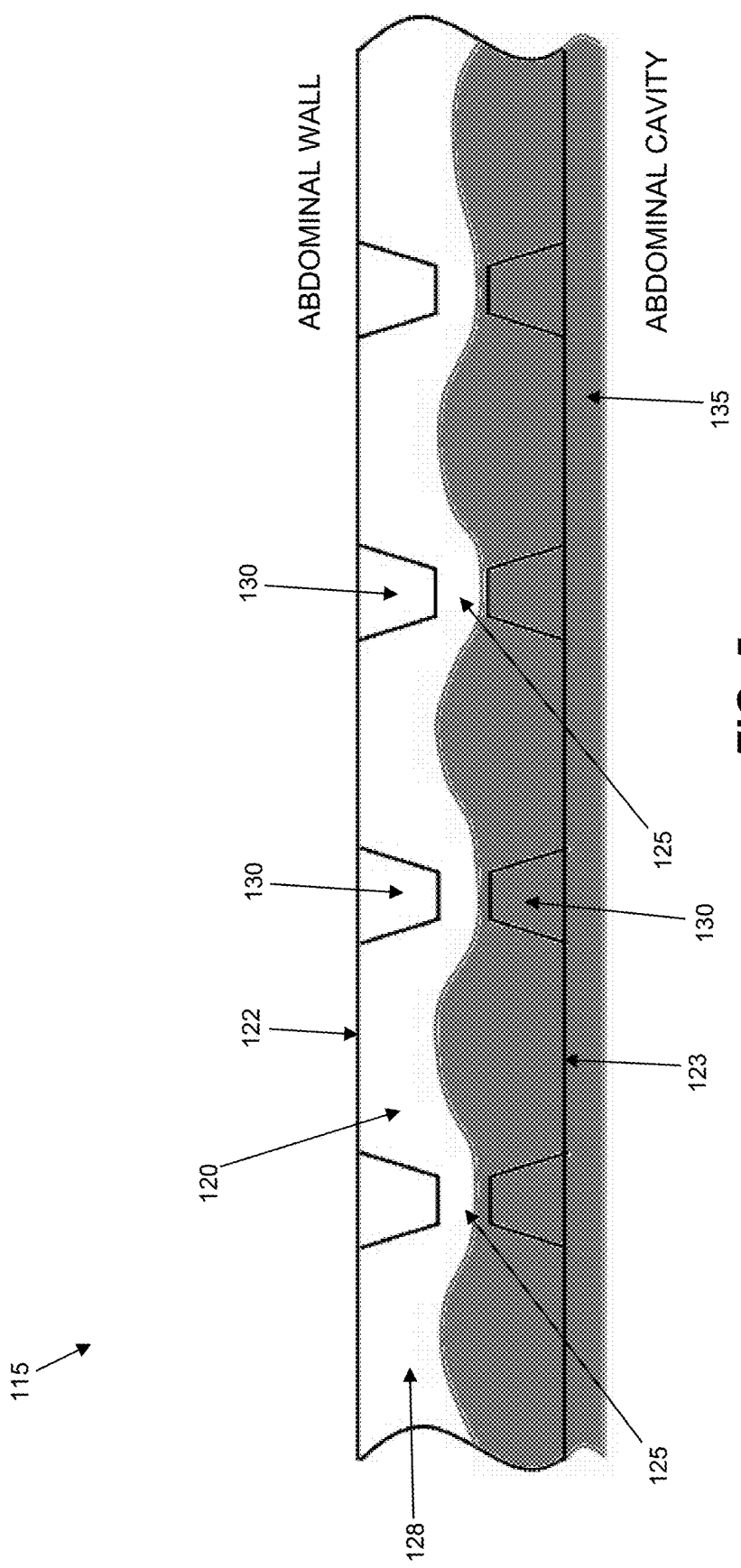
FIG. 5 is a schematic view showing a coated surgical mesh formed in accordance with the present invention, wherein an ingrowth-preventing coating is applied on one side of the surgical mesh and does not penetrate through to the other side of the surgical mesh.
Figure 6:
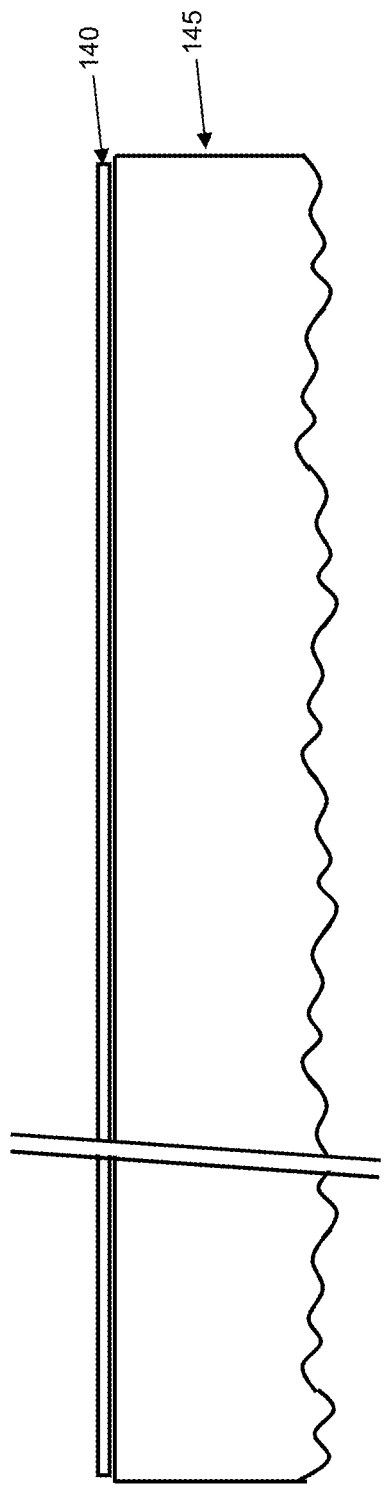
FIGS. 6-10 are schematic views showing how an ingrowth-preventing coating can be applied to one side of the surgical mesh in accordance with the present invention.
Figure 7:
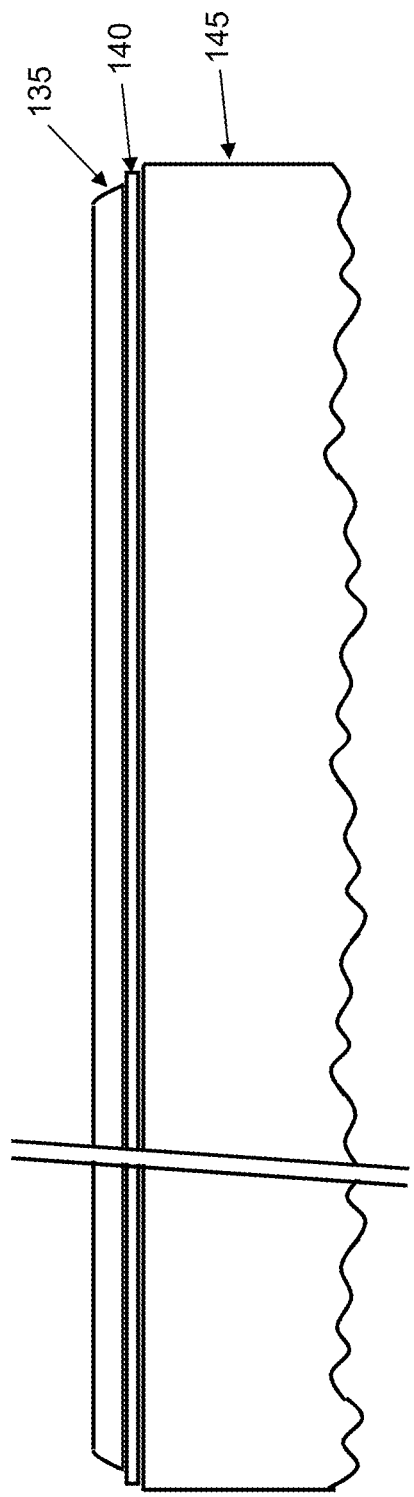
Figure 8:
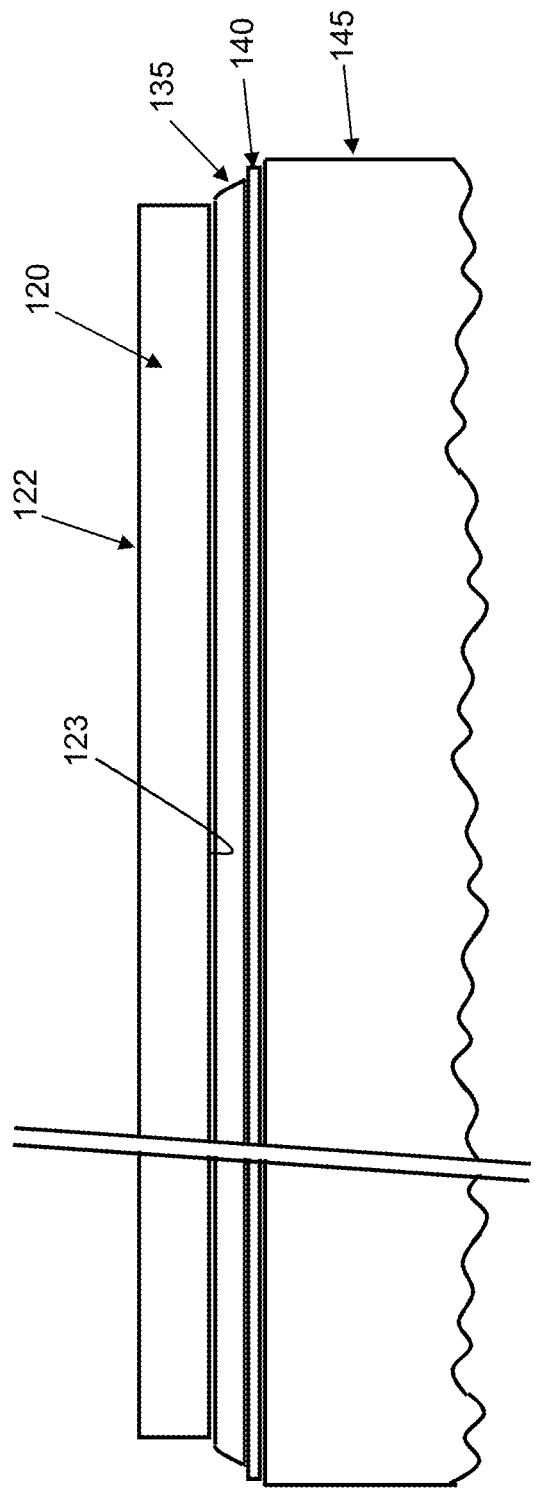
Figure 9:
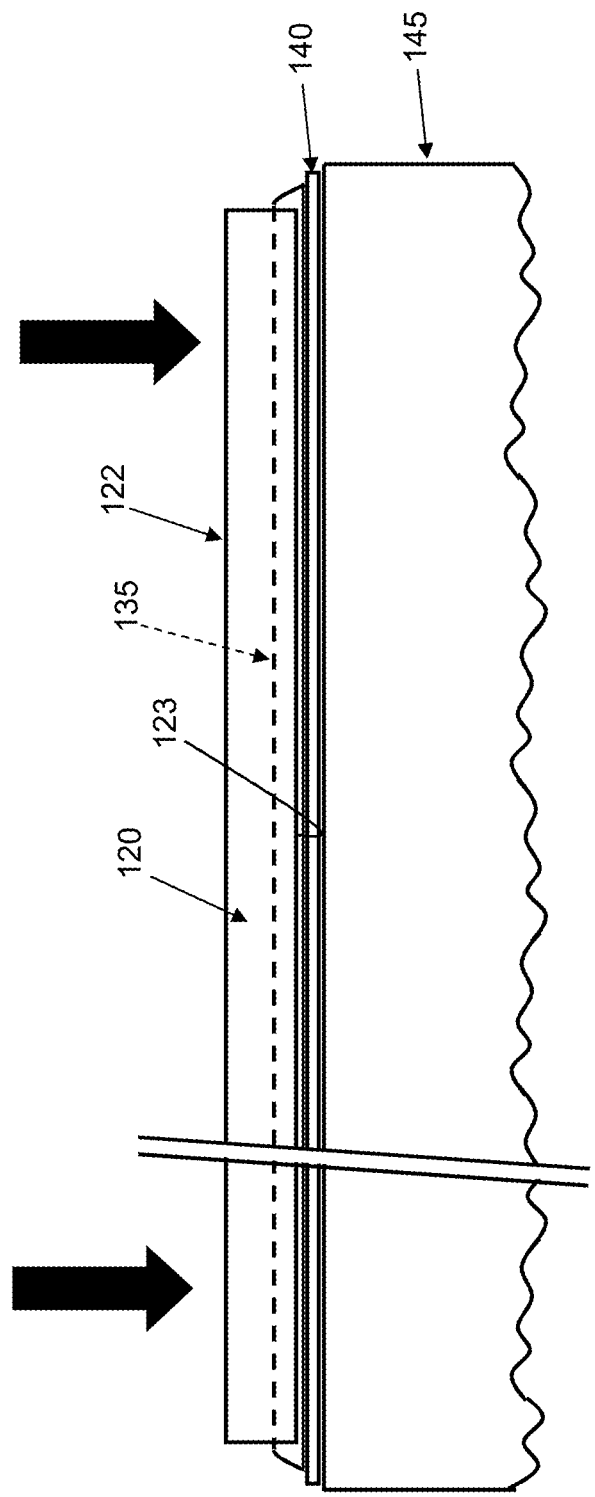

More particularly, and looking now at FIG. 5, there is shown a novel coated surgical mesh 115 formed in accordance with the present invention. In one preferred form of the invention, coated surgical mesh 115 comprises a surgical mesh 120. Surgical mesh 120 generally comprises a first surface 122 which is intended to be adhered to tissue (e.g., to an abdominal wall, in the case of a hernia mesh) and a second surface 123 which is intended to face away from the tissue to which the surgical mesh is adhered (e.g., to face toward an abdominal cavity, in the case of a hernia mesh). By way of example but not limitation, surgical mesh 120 may comprise a non-knitted/non-woven material. In one form of the invention, the non-knitted/non-woven material may comprise a matrix of synthetic fibers (e.g., polypropylene) fused together (e.g., at 125) by a point-bonding fusing process (e.g., by a point-bonding melting) so as to form a composite porous structure. In this respect it will be appreciated that the compressive heat fusion process typically leaves a plurality of regularly-spaced recesses 130 which extend partially into, but not all of the way through, the thickness of the non-knitted/non-woven surgical mesh. It should be appreciated that these recesses 130, extending partially into, but not all the way through, the thickness of the non-knitted/non-woven surgical mesh, constitute only a small percentage of the surface area of the non-knitted/non-woven surgical mesh. Note that the non-knitted/non-woven surgical mesh material disposed at recesses 130 (e.g., at 125) typically has a higher density than the remainder of the non-knitted/non-woven mesh material, since the non-knitted/non-woven surgical mesh material has been compacted and melted in this region of the non-knitted/non-woven surgical mesh.

An ingrowth-preventing coating 135, formed out of a permanent or resorbable non-porous flexible coating (e.g., silicone, urethane, a resorbable material, etc.), is applied to second surface 123 of surgical mesh 120 so as to form the completed coated surgical mesh 115. In accordance with the present invention, ingrowth-preventing coating 135 is applied to surgical mesh 120 in liquid form and is thereafter cured so as to convert ingrowth-preventing coating 135 to a solid form which adheres to surgical mesh 120. Ingrowth-preventing coating 135 does not penetrate through to the other side of surgical mesh 120 (i.e., ingrowth-preventing coating 135 does not penetrate through to first surface 122 of surgical mesh 120). As a result, coated surgical mesh 115 permits tissue ingrowth into first surface 122 of coated surgical mesh 115 (e.g., into the abdominal wall side of the surgical mesh) and prevents tissue ingrowth into second surface 123 of coated surgical mesh 115 (e.g., into the abdominal cavity side of the surgical mesh).

Note that, in the context of the present invention, ingrowth-preventing coating 135 exists in two states: (i) a liquid, flowable state for introduction to, and ingress into, surgical mesh 120, and (ii) a solid, non-flowable state after curing, which adheres to surgical mesh 120 (e.g., by mechanical interlock) so as to form the coated surgical mesh 115.

Thus, in one form of the invention, the ingrowth-preventing coating penetrates into the pores of the surgical mesh while the ingrowth-preventing coating is in a liquid state, and is thereafter cured to a solid state so that the ingrowth-preventing coating mechanically interlocks with the surgical mesh so that the ingrowth-preventing coating and the surgical mesh together form the coated surgical mesh.

Figure 10:
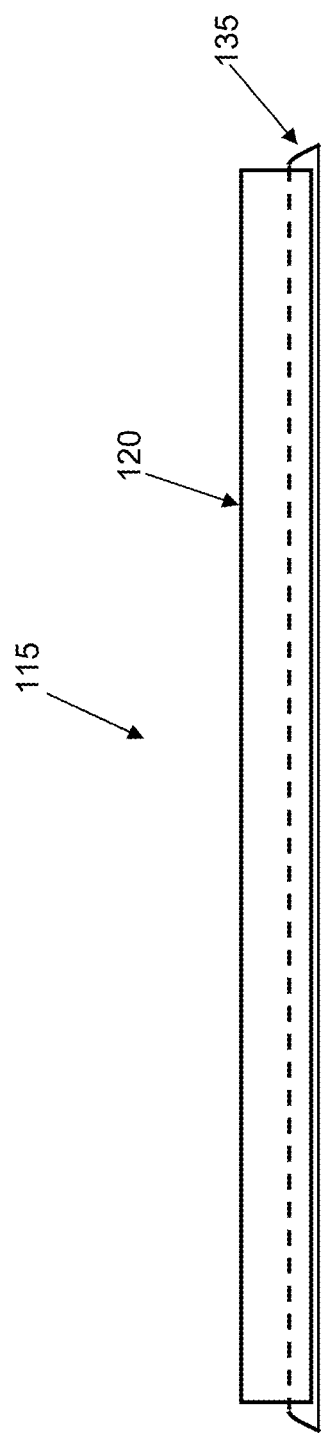
Figure 11:
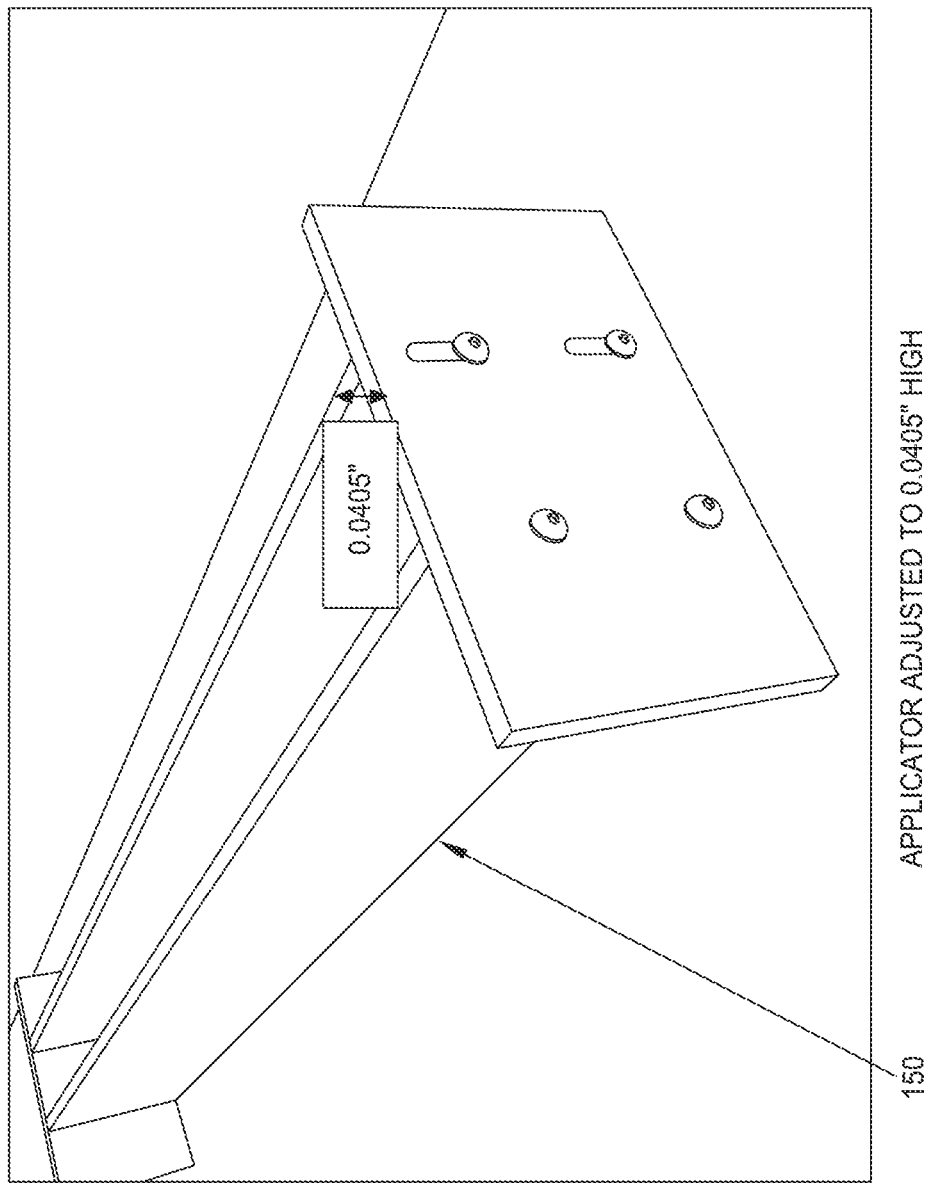
FIGS. 11-19 are schematic views showing a preferred method for applying the ingrowth-preventing coating to one side of the surgical mesh in accordance with the present invention.
Figure 12:
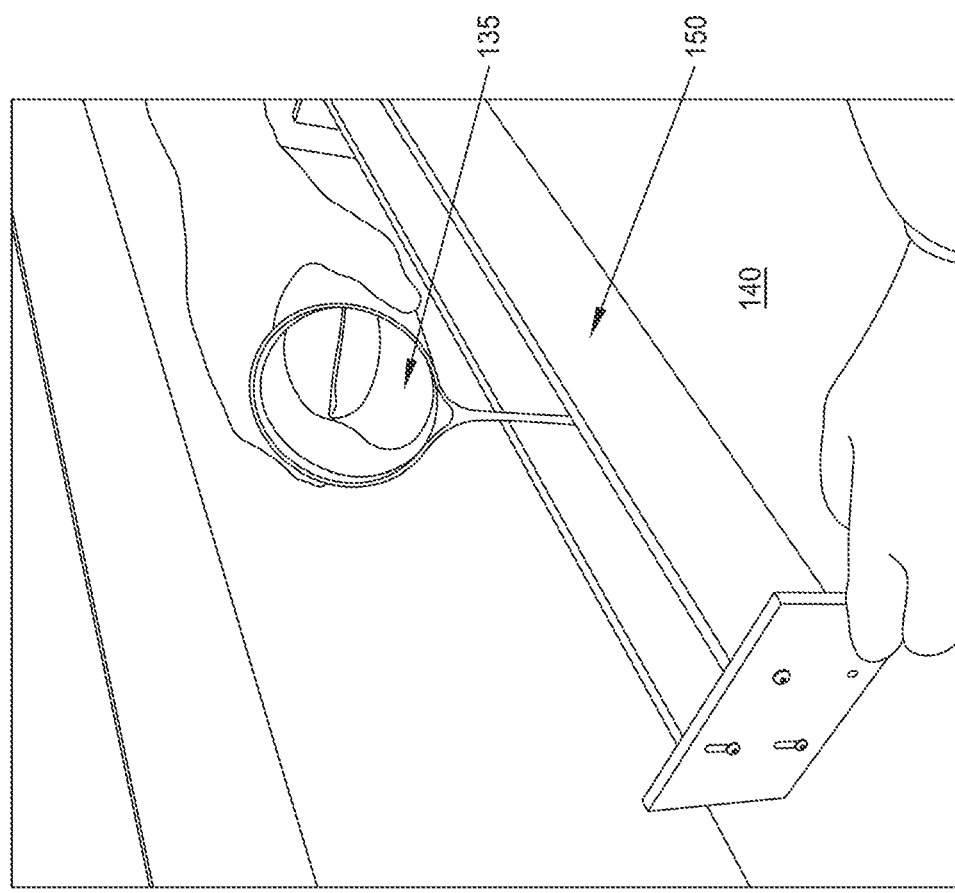
Figure 13:
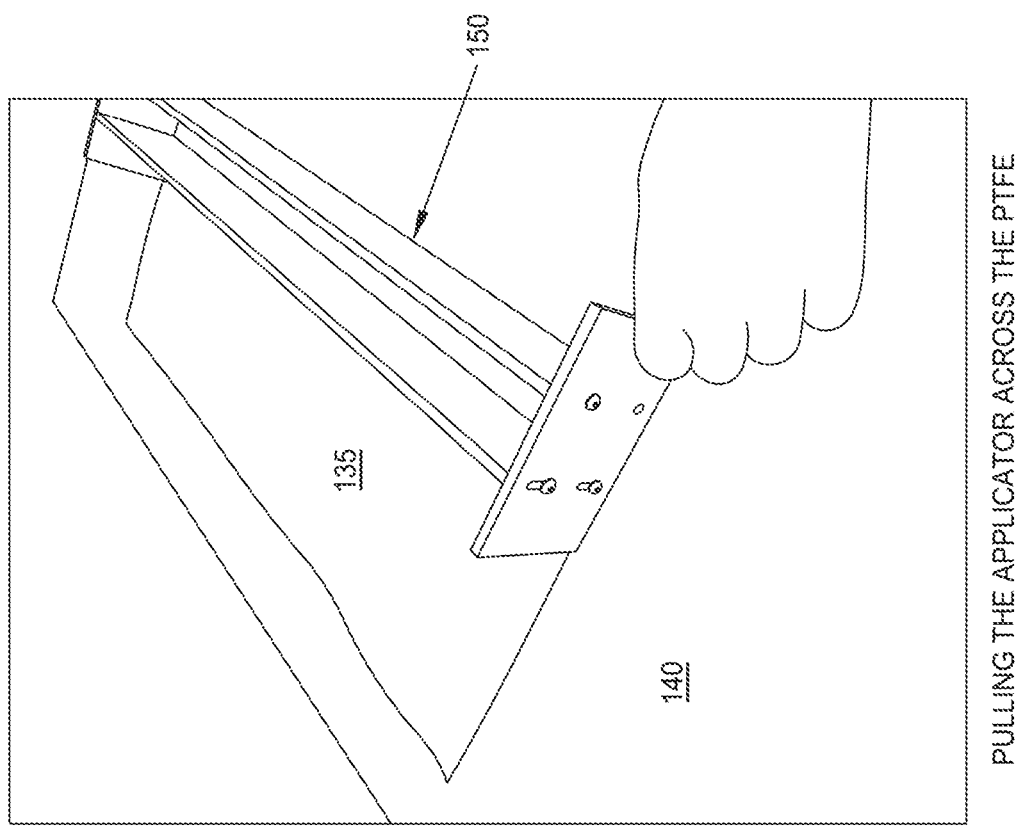
Figure 14:
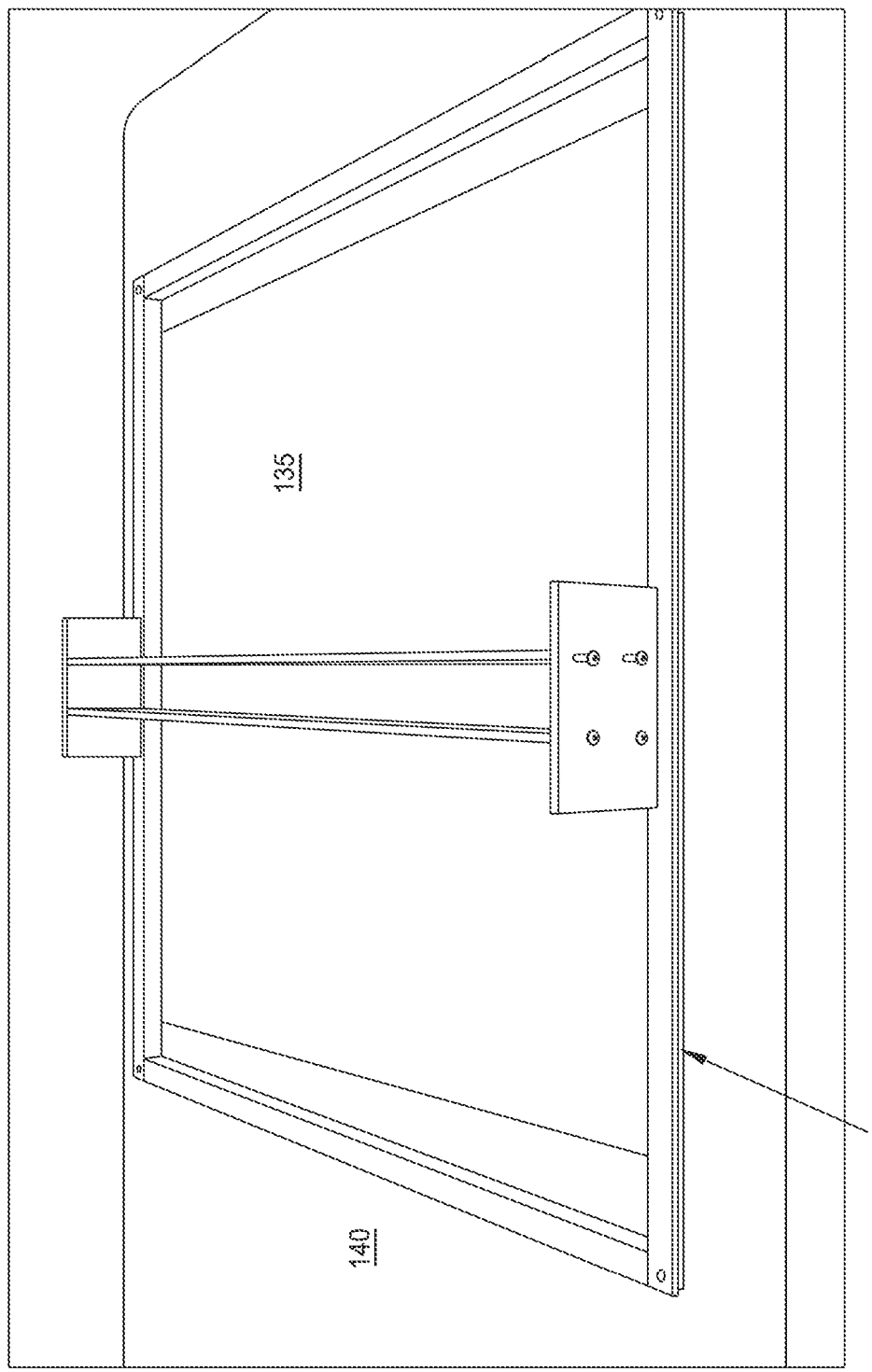
Figure 15:
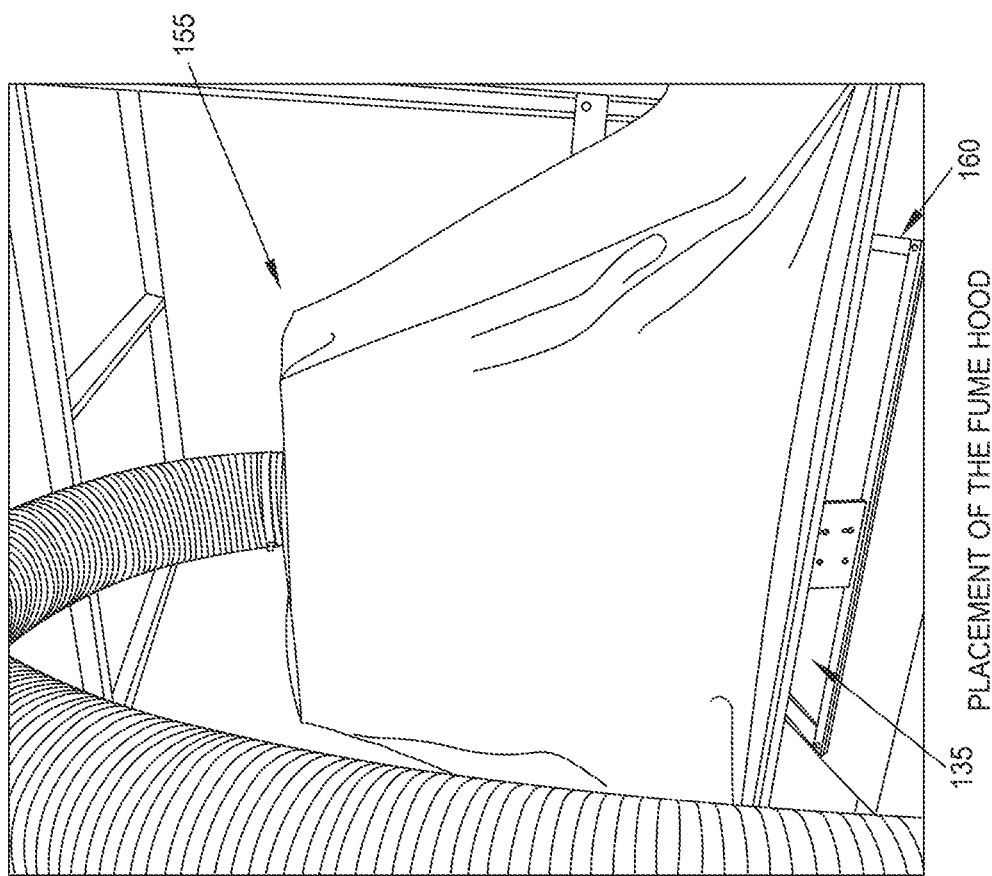
Figure 16:
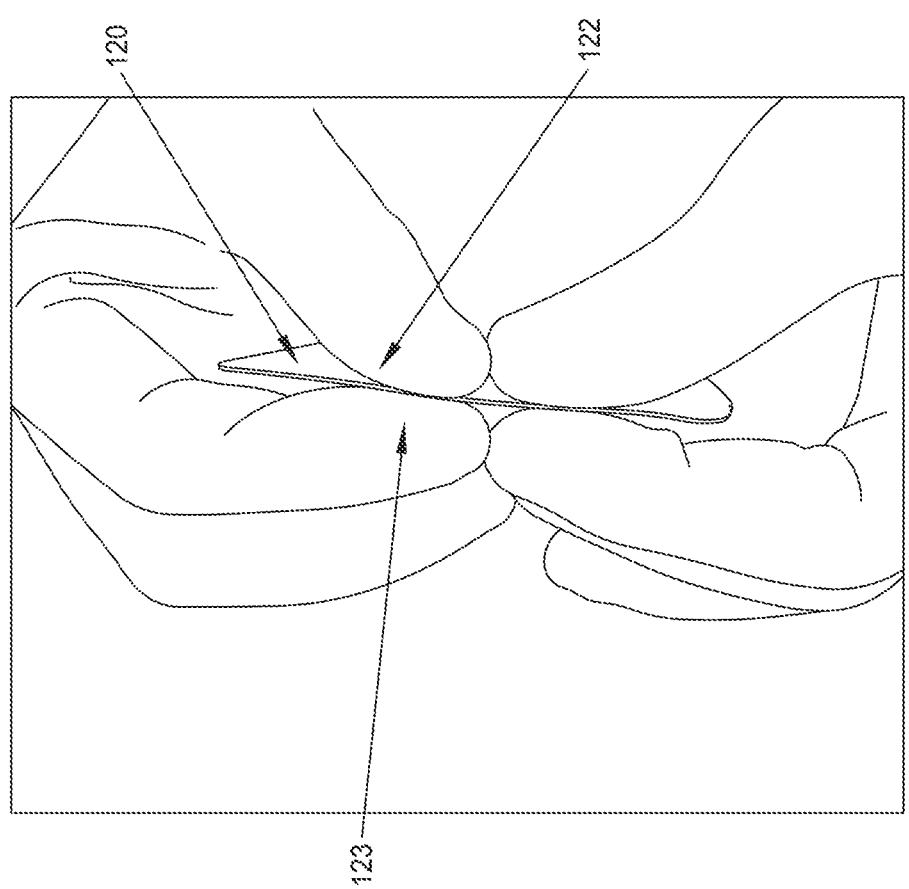
Figure 17:
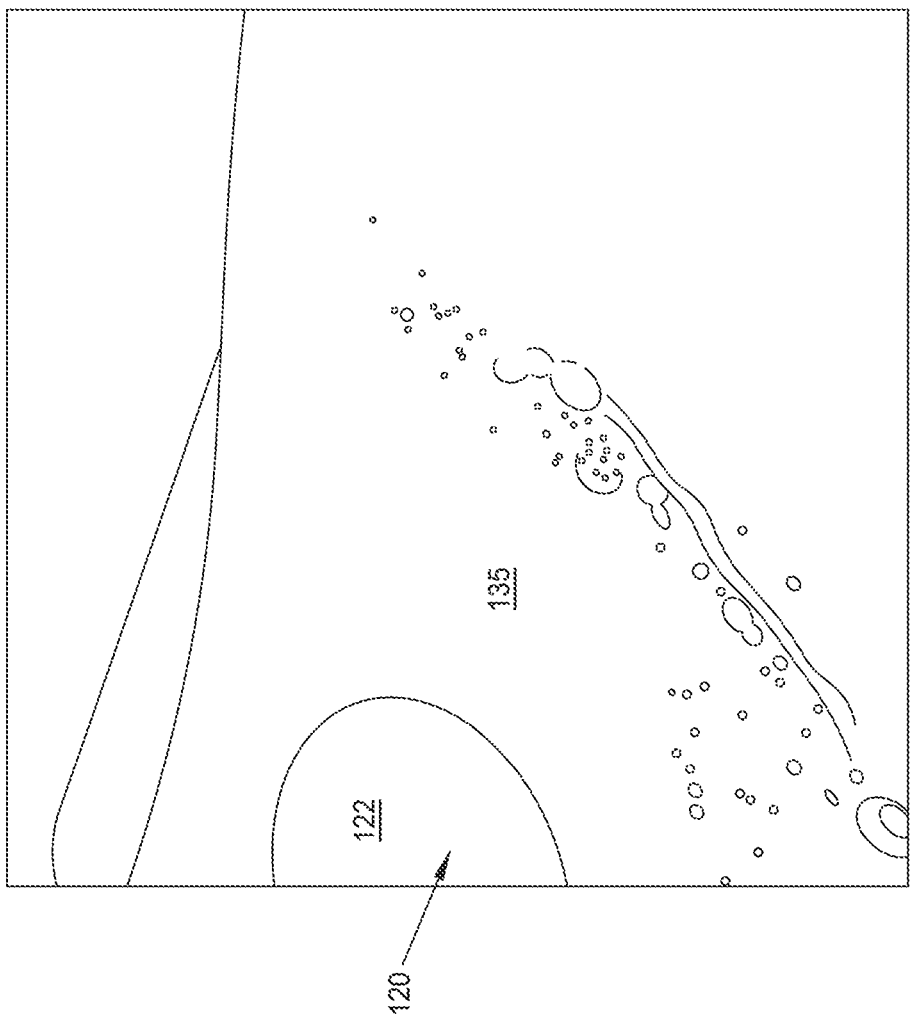
Figure 18:
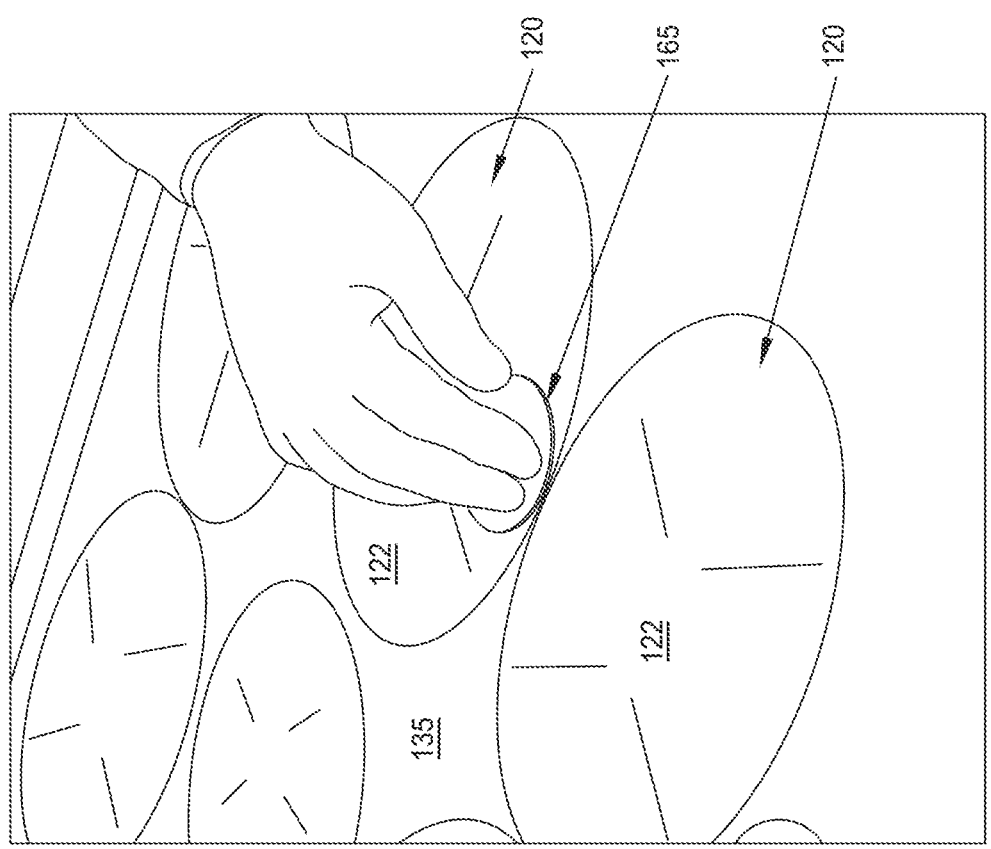
Figure 19:
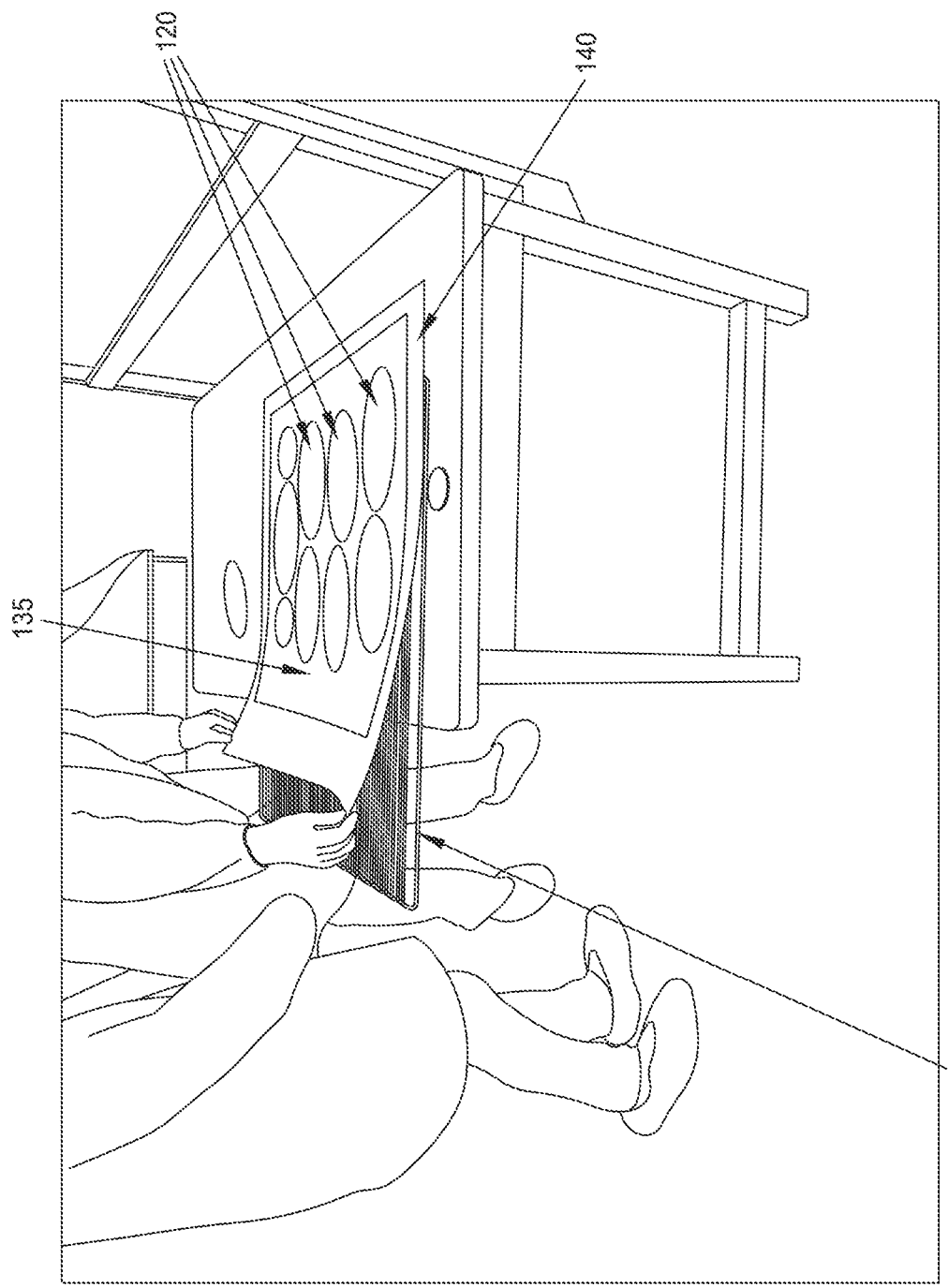

As seen in FIGS. 6-10, coated surgical mesh 115 is manufactured by placing a release sheet 140 onto a tabletop 145 (FIG. 6); positioning ingrowth-preventing coating 135 onto release sheet 140 (FIG. 7); placing second surface 123 of surgical mesh 120 (i.e., the abdominal cavity side of surgical mesh 120) onto the top surface of ingrowth-preventing coating 135 (FIG. 8); applying pressure to first surface 122 of surgical mesh 120 so that ingrowth-preventing coating 135 is forced up into the pores of surgical mesh 120 without penetrating all the way through surgical mesh 120 (FIG. 9); ingrowth-preventing coating 135 is cured so as to fuse the ingrowth-preventing coating to surgical mesh 120, whereby to form coated surgical mesh 115; and then coated surgical mesh 115 is removed from release sheet 140 (FIG. 10).

Thus, in one form of the invention, the ingrowth-preventing coating penetrates into the pores of the surgical mesh while the ingrowth-preventing coating is in a liquid state, and is thereafter cured to a solid state so that the ingrowth-preventing coating mechanically interlocks with the surgical mesh so that the ingrowth-preventing coating and the surgical mesh together form the coated surgical mesh. In one preferred form of the invention, release sheet 140 comprises a sheet of polytetrafluoroethylene (PTFE), commonly sold under the trade name Teflon®.

In one preferred form of the invention, ingrowth-preventing coating 135 comprises a liquid dispersion of silicone which has a desired degree of viscosity and is capable of being cured so as to convert the liquid dispersion of silicone into a solid layer of silicone. The liquid dispersion of silicone may be prepared by thinning the silicone to an appropriate extent using an appropriate organic solvent such as xylene. The viscosity of the liquid dispersion of silicone is such that when the liquid dispersion of silicone is applied to release sheet 140, the liquid dispersion of silicone settles under the influence of gravity so that it has a substantially uniform (i.e., planar) top surface. The liquid dispersion of silicone also has a viscosity such that when surgical mesh 120 has its second surface 123 placed on the top surface of the liquid dispersion of silicone and appropriate weight is applied to first surface 122 of surgical mesh 120, the liquid silicone dispersion penetrates into surgical mesh 120 to a desired extent, but does not penetrate all the way through to first surface 122 of surgical mesh 120 (e.g., the abdominal wall side of surgical mesh 120).

In one preferred form of the present invention, ingrowth-preventing coating 135 penetrates 10-40% of the depth of surgical mesh 120. In another preferred form of the present invention, ingrowth-preventing coating 135 penetrates 40-60% of the depth of surgical mesh 120. In yet another preferred form of the present invention, ingrowth-preventing coating 135 penetrates 60-90% of the depth of surgical mesh 120. It should be appreciated that, inasmuch as compressed portions 125 of surgical mesh 120 have a higher density than the remainder of the surgical mesh, ingrowth-preventing coating 135 penetrates these compressed portions 125 to a lesser degree.

In one preferred form of the invention, ingrowth-preventing coating 135 is cured by the application of appropriate heat, UV irradiation, drying, a catalyst, gamma radiation, etc. so that ingrowth-preventing coating 135 is converted from its liquid form to its solid form and adheres to surgical mesh 120 so as to form coated surgical mesh 115. In one form of the present invention, curing is achieved by a combination of the foregoing, e.g., by the application of appropriate heat and a catalyst.

Thus, in one form of the invention, the ingrowth-preventing coating penetrates into the pores of the surgical mesh while the ingrowth-preventing coating is in a liquid state, and is thereafter cured to a solid state so that the ingrowth-preventing coating mechanically interlocks with the surgical mesh so that the ingrowth-preventing coating and the surgical mesh together form the coated surgical mesh.

It should be appreciated that, by virtue of the foregoing approach, the degree to which the ingrowth-preventing coating 135 penetrates surgical mesh 120 can be controlled by varying:

(i) the composition and construction of surgical mesh 120;
(ii) the composition of ingrowth-preventing coating 135;
(iii) the pressure applied to first surface 122 of surgical mesh 120; and
(iv) the curing parameters of ingrowth-preventing coating 135.

In any case, ingrowth-preventing coating 135 forms a substantially complete coating on second surface 123 of surgical mesh 120 (e.g., on the abdominal cavity side of the surgical mesh) and does not penetrate through to first surface 122 of surgical mesh 120 (e.g., to the abdominal wall side of the surgical mesh).

It should also be appreciated that ingrowth-preventing coating 135 may be formed by resorbable elastomers well known in the art of polymer chemistry. By way of example but not limitation, ingrowth-preventing coating 135 may comprise at least one from the group consisting of polytrimethylcarbonate, polycaprolactone, polydioxanone and polybutyleneterephthalate. Additionally, the aforementioned resorbable polymers may also be mixed with other resorbable materials well known in the art such as polylactic acid (PLA) and/or polyglycolic acid (PGA) in order to optimize certain properties of the ingrowth-preventing coating (e.g., the strength of the coating, the stiffness of the coating, the resorption properties of the coating, etc.).

Thus it will be seen that the present invention may be used to provide a novel coated surgical mesh having a well-controlled, substantially flat, tissue ingrowth-preventing coating on one side of the surgical mesh (e.g., the abdominal cavity side of the surgical mesh) and a porous, tissue ingrowth-promoting surface on the opposite side of the surgical mesh (e.g., the abdominal wall side of the surgical mesh).

Preferred Method of Manufacture

In one preferred form of the invention, and looking now at FIGS. 11-19, ingrowth-preventing coating 135 is adhered to surgical mesh 120 in the following manner so as to produce coated surgical mesh 115.

1. Equipment And Supplies Used
1.1 Silicone applicator 150 (see FIG. 11)
1.2 Fumehood 155 (see FIG. 15)
1.3 Curing oven (not shown)
1.4 release sheet 140 (PTFE sheet)
1.5 Scale (not shown)
1.6 Pin gauge set (not shown)
1.7 100 mL beakers (not shown)
1.8 300 mL beaker (not shown)
1.9 Frame 160 (see FIG. 14)
1.10 Flattening piece 165 (see FIG. 18)
1.11 Oven rack 170 (see FIG. 19)
2. Materials
2.1 Surgical mesh 120 (porous non-knitted/non-woven material)
2.2 Ingrowth-preventing coating 135 (liquid silicone dispersion, 2 part, heat curable silicone dispersion, Nusil™ MED-6600, sold by Nusil Technology LLC of Carpinteria, Calif., USA, Part A and Part B both containing silicone and xylene)
3. Procedure
3.1 Set up silicone applicator 150—Using a pin gauge, set the height of the opening on the silicone applicator to an appropriate setting, e.g., 0.0405 inch. See FIG. 11. The height of the opening on the silicone applicator will establish the thickness of the layer of ingrowth-preventing coating 135 which will be deposited on release sheet 140 (i.e., the PTFE sheet).

3.2 Silicone Application—Using the scale, measure 120.0 grams of Part A of the Nusil™ MED-6600 and Part B of the Nusil™ MED-6600 in 2 separate beakers.

3.3 Combine Parts A and B of the Nusil™ MED-6600 in the 300 ml beaker and stir the material.

3.4 Place silicone applicator 150 onto release sheet 140 (i.e., the PTFE sheet) so that ingrowth-preventing coating 135 will flow out of silicone applicator 150 and onto release sheet 140 when silicone applicator 150 is slid across release sheet 140 (i.e., the PTFE sheet).

3.5 Pour ingrowth-preventing coating 135 into silicone applicator 150. See FIG. 12.

3.6 Slide silicone applicator 150 over release sheet 140 (i.e., the PTFE sheet) so that ingrowth-preventing coating 135 is dispersed onto release sheet 140 (i.e., the PTFE sheet). See FIG. 13. The ingrowth-preventing coating 135 deposited onto release sheet 140 (i.e., the PTFE sheet) will have a thickness set by the opening on the silicone applicator (e.g., 0.0405 inch).

3.7 After ingrowth-preventing coating 135 is spread onto release sheet 140 (i.e., the PTFE sheet), silicone applicator 150 is removed. Note that the viscosity of ingrowth-preventing coating 135 is such that ingrowth-preventing coating 135 settles under the influence of gravity so as to have a substantially uniform (i.e., planar) top surface.

3.8 Place frame 160 around the edges of the dispersed ingrowth-preventing coating 135 to help hold release sheet 140 (i.e., the PTFE sheet) flat. See FIG. 14.

3.9 Place fumehood 155 over release sheet 140 (i.e., the PTFE sheet) and let the solvent in ingrowth-preventing coating 135 evaporate for 2 hours. See FIG. 15.

3.10 To determine if ingrowth-preventing coating 135 is ready for use (i.e., ready to be adhered to surgical mesh 120), gently poke the edge of ingrowth-preventing coating 135 so as to form a poke mark. If the poke mark is still visible after 5 minutes, the ingrowth-preventing coating 135 is ready for use. If ingrowth-preventing coating 135 is not yet ready for use, allow ingrowth-preventing coating 135 to sit for an additional 0.5 hours and then re-test ingrowth-preventing coating 135.

3.11 Place second surface 123 of surgical mesh 120 onto ingrowth-preventing coating 135. See FIG. 16. Do not place second surface 123 of surgical mesh 120 onto any bubbles which may be present in ingrowth-preventing coating 135. See FIG. 17.

3.12 Once second surface 123 of surgical mesh 120 is placed onto ingrowth-preventing coating 135, flattening piece 165 is used to lightly slide surgical mesh 120 around the surface of ingrowth-preventing coating 135 so as to ensure ingrowth-preventing coating 135 is absorbing into second surface 123 of surgical mesh 120. Flattening piece 165 is not used to push down surgical mesh 120, it is just used to ensure that second surface 123 of surgical mesh 120 is in full contact with ingrowth-preventing coating 135. See FIG. 18.

3.13 Allow surgical mesh 120 to sit atop ingrowth-preventing coating 135 for 15 minutes. Inspect the edges of surgical mesh 120 after the 15 minutes to confirm that surgical mesh 120 remains flat on ingrowth-preventing coating 135. If an edge of surgical mesh 120 is coming off ingrowth-preventing coating 135, use flattening piece 165 again to smooth surgical mesh 120 onto ingrowth-preventing coating 135.

3.14 Apply weights (not shown) to first surface 122 of surgical mesh 120. The specific amount of weight applied to first surface 122 of surgical mesh 120 will determine the extent to which ingrowth-preventing coating 135 penetrates through second surface 123 of surgical mesh 120 and into surgical mesh 120 (e.g., 10%, 20%, 30%, etc.).

3.15 Slide release sheet 140 (i.e., the PTFE sheet), which is carrying ingrowth-preventing coating 135 and surgical mesh 120, onto oven rack 170. See FIG. 19.

3.16 Place release sheet 140 (i.e., the PTFE sheet), which is carrying ingrowth-preventing coating 135 and surgical mesh 120, into the oven. Set the oven temperature to 160° F., and leave release sheet 140 (i.e., the PTFE sheet), which is carrying ingrowth-preventing coating 135 and surgical mesh 120, in the oven for 45 minutes.

3.17 After the 45 minutes have passed, increase the temperature of the oven to 292° F. and leave release sheet 140 (i.e., the PTFE sheet), which is carrying ingrowth-preventing coating 135 and surgical mesh 120, in the oven for 2.5 hours. At this point, ingrowth-preventing coating 135 will have been cured to a solid form and secured to surgical mesh 120, whereby to form coated surgical mesh 115. Thus, in one form of the invention, the ingrowth-preventing coating penetrates into the pores of the surgical mesh while the ingrowth-preventing coating is in a liquid state, and is thereafter cured to a solid state so that the ingrowth-preventing coating mechanically interlocks with the surgical mesh so that the ingrowth-preventing coating and the surgical mesh together form the coated surgical mesh.

3.18 After the 2.5 hours have passed, shut off the oven and allow release sheet 140 (i.e., the PTFE sheet), which is carrying coated surgical mesh 115, to cool for 30 minutes inside the oven. Once cool, remove release sheet 140 (i.e., the PTFE sheet), which is carrying coated surgical mesh 115, and set onto a flat table.

3.19 Starting at one corner, slowly peel off coated surgical mesh 115 from release sheet 140 (i.e., the PTFE sheet). Place coated surgical mesh 115 on a cutting mat (not shown). Using a scalpel (not shown), trim around the edges of coated surgical mesh 115. Note that trimming around the edges of coated surgical mesh 115 should be done as close as possible to coated surgical mesh 115 without cutting coated surgical mesh 115.

3.20 Inspect coated surgical mesh 115 to ensure ingrowth-preventing coating 135 is adhered to surgical mesh 120 at all locations. Also ensure that the edges of coated surgical mesh 115 are coated with ingrowth-preventing coating 135.

Thus it will be seen that, using the preferred method of manufacture discussed above, an ingrowth-preventing coating 135: (i) is applied to second surface 123 of surgical mesh 120 so as to form the completed coated surgical mesh 115; (ii) is applied to surgical mesh 120 in liquid form and is thereafter cured so as to convert ingrowth-preventing coating 135 to a solid form which adheres to surgical mesh 120; and (iii) does not penetrate through to the other side of surgical mesh 120 (i.e., ingrowth-preventing coating 135 does not penetrate through to first surface 122 of surgical mesh 120).

As a result, coated surgical mesh 115 permits tissue ingrowth into first surface 122 of coated surgical mesh 115 (e.g., into the abdominal wall side of the surgical mesh) and prevents tissue ingrowth into second surface 123 of coated surgical mesh 115 (e.g., into the abdominal cavity side of the surgical mesh).

Use of the Present Invention with Knitted/Woven Surgical Meshes

It should be appreciated that the present invention may also be utilized with knitted/woven surgical meshes. In this case, the ingrowth-preventing coating (e.g., a permanent or resorbable non-porous flexible coating such as silicone, urethane, a flexible resorbable material, etc., preferably thinned with an appropriate solvent) is applied using the aforementioned technique of FIGS. 6-10 to the second surface of the knitted/woven surgical mesh and then cured, so that the ingrowth-preventing coating forms a substantially complete coating on the second surface of the knitted/woven surgical mesh (e.g., on the abdominal cavity side of the knitted/woven surgical mesh) and does not penetrate through to the first surface of the knitted/woven surgical mesh.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method of manufacturing a coated surgical mesh, said method comprising:
providing a surgical mesh comprising a first surface and a second surface, wherein the surgical mesh comprises a non-knitted/non-woven material;
providing a release sheet;
positioning an ingrowth-preventing coating onto the release sheet, wherein the ingrowth-preventing coating comprises a liquid dispersion of silicone;
allowing the ingrowth-preventing coating to settle on the release sheet under the influence of gravity so that the ingrowth-preventing coating has a substantially planar top surface;
placing the second surface of the surgical mesh onto the ingrowth-preventing coating;
applying pressure to the first surface of the surgical mesh so that the ingrowth-preventing coating is forced into the surgical mesh without penetrating all the way through the surgical mesh to the first surface of the surgical mesh;
curing the ingrowth-preventing coating so as to fuse the ingrowth-preventing coating to the surgical mesh, whereby to form the coated surgical mesh; and
removing the coated surgical mesh from the release sheet.

2. A method according to claim 1 wherein the non-knitted/non-woven material comprises a polymer.

3. A method according to claim 2 wherein the non-knitted/non-woven material comprises polypropylene.

4. A method according to claim 1 wherein the viscosity of the liquid dispersion of silicone can be decreased by adding an organic solvent to the liquid dispersion of silicone whereby to control the percentage of tissue ingrowth on the first surface of the surgical mesh.

5. A method according to claim 4 wherein the organic solvent is xylene.

6. A method according to claim 4 wherein the ingrowth-preventing coating penetrates 10-20% of the depth of the surgical mesh so as to allow for 90-80% tissue ingrowth on the first surface of the surgical mesh.

7. A method according to claim 4 wherein the ingrowth-preventing coating penetrates 20-40% of the depth of the surgical mesh so as to allow for 80-60% tissue ingrowth on the first surface of the surgical mesh.

8. A method according to claim 4 wherein the ingrowth-preventing coating penetrates 40-60% of the depth of the surgical mesh so as to allow for 60-40% tissue ingrowth on the first surface of the surgical mesh.

9. A method according to claim 1 wherein the ingrowth-preventing coating cures to a flexible solid.

10. A method according to claim 1 wherein the step of curing comprises at least one from the group consisting of the application of heat, ultra-violet irradiation, drying, a catalyst, and gamma radiation.

11. A method according to claim 1 wherein the step of curing comprising a combination of applying heat and a catalyst.

12. A method according to claim 1 wherein the release sheet comprises polytetrafluoroethylene (PTFE).

13. A method according to claim 1 further comprising trimming the coated surgical mesh after removing the coated surgical mesh from the release sheet.

14. A method according to claim 1 wherein the step of applying pressure to the first surface of the surgical mesh comprises adding weights to the first surface of the surgical mesh.

15. A method of manufacturing a coated surgical mesh, said method comprising:
providing a surgical mesh comprising a first surface and a second surface, wherein the surgical mesh comprises a non-knitted/non-woven material;
providing a release sheet;
positioning an ingrowth-preventing coating comprising a liquid dispersion of silicone onto the release sheet using an applicator;
allowing the ingrowth-preventing coating to evaporate for a period of time;
placing the second surface of the surgical mesh onto the ingrowth-preventing coating;
using a flattening piece to slide the surgical mesh around the ingrowth-preventing coating without pushing down on the surgical mesh;
applying pressure to the first surface of the surgical mesh so that the ingrowth-preventing coating is forced into the surgical mesh without penetrating all the way through the surgical mesh to the first surface of the surgical mesh;
curing the ingrowth-preventing coating so as to fuse the ingrowth-preventing coating to the surgical mesh, whereby to form the coated surgical mesh;
removing the coated surgical mesh from the release sheet; and
trimming around the coated surgical mesh.

16. A method according to claim 15 wherein the non-knitted/non-woven material comprises a polymer.

17. A method according to claim 16 wherein the non-knitted/non-woven material comprises polypropylene.

18. A method according to claim 15 wherein the viscosity of the liquid dispersion of silicone can be decreased by adding an organic solvent to the liquid dispersion of silicone whereby to control the percentage of tissue ingrowth on the first surface of the surgical mesh.

19. A method according to claim 18 wherein the organic solvent is xylene.

20. A method according to claim 18 wherein the ingrowth-preventing coating penetrates 10-20% of the depth of the surgical mesh so as to allow for 90-80% tissue ingrowth on the first surface of the surgical mesh.

21. A method according to claim 18 wherein the ingrowth-preventing coating penetrates 20-40% of the depth of the surgical mesh so as to allow for 80-60% tissue ingrowth on the first surface of the surgical mesh.

22. A method according to claim 18 wherein the ingrowth-preventing coating penetrates 40-60% of the depth of the surgical mesh so as to allow for 60-40% tissue ingrowth on the first surface of the surgical mesh.

23. A method according to claim 15 wherein the ingrowth-preventing coating cures to a flexible solid.

24. A method according to claim 15 wherein the step of curing comprises at least one from the group consisting of the application of heat, ultra-violet irradiation, drying, a catalyst, and gamma radiation.

25. A method according to claim 15 wherein the step of curing comprising a combination of applying heat and a catalyst.

26. A method according to claim 15 wherein the release sheet comprises polytetrafluoroethylene (PTFE).

27. A method according to claim 15 further comprising trimming the coated surgical mesh after removing the coated surgical mesh from the release sheet.

28. A method according to claim 15 wherein the step of applying pressure to the first surface of the surgical mesh comprises adding weights to the first surface of the surgical mesh.

\* \* \* \* \*